(12) United States Patent  
Reilly

(10) Patent No.: US 7,637,164 B1
(45) Date of Patent: Dec. 29, 2009

(54) APPARATUS FOR COMPARATIVE PRESSURE MEASUREMENTS OF SELF-CONTAINED BREATHING APPARATUSES

(76) Inventor: Kevin J. Reilly, 130 N. Maple Ave., Ridgewood, NJ (US) 07450

( * ) Notice: Subject to any disclaimer, the term of this patent is extended or adjusted under 35 U.S.C. 154(b) by 0 days.

(21) Appl. No.: 12/041,198

(22) Filed: Mar. 3, 2008

Related U.S. Application Data

(60) Provisional application No. 60/892,544, filed on Mar. 2, 2007.

(51) Int. Cl.
*G01L 7/00* (2006.01)
(52) U.S. Cl. ..................................... 73/700; 128/200.24
(58) Field of Classification Search ........... 73/700–756; 128/200.24–207.29
See application file for complete search history.

(56) References Cited

U.S. PATENT DOCUMENTS

| | | | |
|---|---|---|---|
| 4,387,600 A | | 6/1983 | Kranz |
| 4,498,471 A | * | 2/1985 | Kranz et al. ............ 128/204.26 |
| 5,097,826 A | | 3/1992 | Gray et al. |
| 5,913,307 A | * | 6/1999 | Taieb et al. ............ 128/205.23 |
| 6,032,664 A | * | 3/2000 | Gray et al. ............. 128/201.27 |
| 6,123,074 A | * | 9/2000 | Hete et al. ............. 128/205.11 |
| 6,148,816 A | * | 11/2000 | Heinonen et al. ...... 128/205.24 |
| 6,253,764 B1 | * | 7/2001 | Calluaud ............... 128/204.18 |
| 6,899,101 B2 | * | 5/2005 | Haston et al. .......... 128/204.26 |
| 7,089,930 B2 | * | 8/2006 | Adams et al. .......... 128/201.27 |
| 7,207,328 B1 | * | 4/2007 | Altemus ................ 128/202.28 |

* cited by examiner

*Primary Examiner*—Lisa M Caputo
*Assistant Examiner*—Jermaine Jenkins
(74) *Attorney, Agent, or Firm*—Hoffmann & Baron, LLP

(57) ABSTRACT

An air gauge assembly is provided herein which allows for accurate comparative pressure measurements between SCBA's. Such precise measurements provide a highly accurate indication of air volume in an air tank of a SCBA; higher pressures mean more air, while lower pressures mean less air. The air gauge assembly includes a mounting member from which extends a pressure line terminating at an adjustable bleeder valve. The mounting member is formed to be mountable to air part of a SCBA. A pressure gauge is mounted along the pressure line which preferably includes a transducer and digital display. The pressure gauge is calibrated to provide a highly accurate reading of pressure in the pressure line. Advantageously, with the device of the subject invention, accurate pressure readings of single or multiple SCBA's may be obtained to not only monitor air volumes therein, but also to permit comparative testing. Such testing may include the testing of breathing techniques of different firefighters.

9 Claims, 1 Drawing Sheet

APPARATUS FOR COMPARATIVE PRESSURE MEASUREMENTS OF SELF-CONTAINED BREATHING APPARATUSES

CROSS-REFERENCE TO RELATED APPLICATION

This application claims priority to U.S. Provisional Application No. 60/892,544, filed Mar. 2, 2007, the entire contents of which are hereby incorporated by reference.

BACKGROUND OF THE INVENTION

Self-contained breathing apparatuses (SCBA's) are well-known in the art. These devices are used extensively by firefighters in fire fighting. To ensure safety in use, both the integrity of the equipment and a person's ability to use the equipment must be continuously monitored and tested.

SCBA's are all equipped with pressure gauges to permit a user to monitor the remaining volume of available air in the air tank. Although digital displays for pressure gauges have been provided, analog gauges are most commonly used. Regardless of the types of pressure gauges mounted to the apparatus itself, the gauges are relatively crude in that precise measurements are generally not provided. Precision in these devices is sacrificed for durability and toughness due to exposure to hazardous environments.

Firefighters are issued a low air alarm as standard equipment. The low air alarm provides an indication that a SCBA is at a dangerously low level of air. Firefighters are trained to call for help upon activation of the low air alarm because insufficient air may be present to provide for proper escape from a fire or hazardous situation. The NFPA (National Fire Protection Association) has tracked non-heart related deaths of firefighters inside structure fires since 1978 and has found that smoke inhalation has been the number one cause of death each year since that time.

A major reason for smoke inhalation deaths among firefighters is the unexpected depletion of air supply. In spite of being provided with various gauges and alarms, a firefighter may deplete an air supply much faster than anticipated. Standard firefighter SCBA's are issued as 30-minute or 45-minute supplies, and, as such, a time element is associated with air supply. However, an actual air supply may only last two-thirds of the allotted time. The shortage of air supply may be attributed to insufficient filling, particularly where errant pressure gauges are used, showing a higher pressure lever than actual (higher pressure reading indicates higher volume of air). Likewise, filling at elevated temperature may present a higher pressure level than actual, with a cooling of the air to ambient providing a lower than expected air volume. Filling SCBA's in succession may lead to filling equipment becoming hot and thrown off pressure measurements. In addition, a firefighter's mask may have a poor seal, causing undesired leakage, and the actual physical condition and breathing technique of the firefighter must be also taken into consideration.

Breathing methods have been developed in the prior art to prolong a SCBA air supply. One such technique known as "skip breathing" calls for intermittently holding one's breath during respiration. However, this technique has been found to increase levels of carbon dioxide in one's blood and is of questionable value. A more effective technique has been developed known as the Reilly-Emergency Breathing Technique (R-EBT) which involves normal inhalation, but humming upon exhalation. This technique has been practiced by firefighters and effective extension of SCBA air supply has been found. In particular, under same use conditions by the same firefighters, it has been found that the R-EBT technique allows for a fixed air supply to last longer than with a normal breathing technique. To allow for effective use for this breathing technique, as well as any other breathing technique, comparative testing and training must be conducted wherein firefighters may be tested against their own results, as well as, the results of others.

Cascade systems and manifold carts are known in the art for simultaneously filling several SCBA's. However, residual pressure in the manifold causes SCBA-to-SCBA pressure fluctuation especially upon sequential closing of the SCBA's. As such, these prior art systems do not permit accurate equal filling amongst a plurality of SCBA's. Without equal filling, a base line for comparative testing cannot be established.

SUMMARY OF THE INVENTION

An air gauge assembly is provided herein which allows for accurate comparative pressure measurements between SCBA's. Such precise measurements provide a highly accurate indication of air volume in an air tank of a SCBA; higher pressures mean more air, while lower pressures mean less air. The air gauge assembly includes a mounting member from which extends a pressure line terminating at an adjustable bleeder valve. The mounting member is formed to be mountable to an air port of a SCBA. A pressure gauge is mounted along the pressure line which preferably includes a transducer and digital display. The pressure gauge is calibrated to provide a highly accurate reading of pressure in the pressure line. Advantageously, with the device of the subject invention, accurate pressure readings of single or multiple SCBA's may be obtained to not only monitor air volumes therein, but also to permit comparative testing. Such testing may include the testing of breathing techniques of different firefighters.

These and other features of the subject invention will be better understood through a study of the following detailed description and accompanying drawings.

DESCRIPTION OF THE INVENTION

Figure 1:
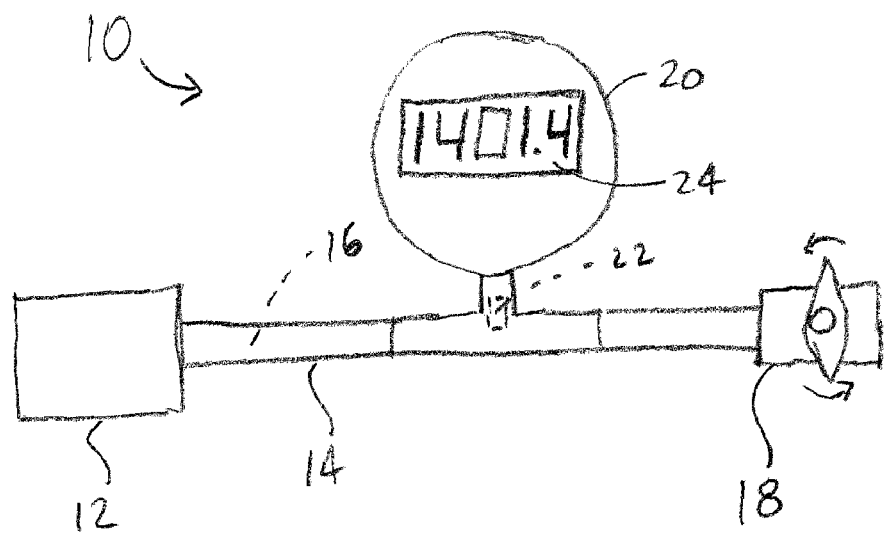
FIG. 1 is a schematic of the subject invention.

With reference to FIG. 1, an air gauge assembly 10 is provided which generally includes a mounting member 12 and a pressure line 14 extending therefrom. The mounting member 12 may include threads or other connecting arrangements (e.g., a "quick connect" coupling) configured to securely mount onto a fitting, particularly an air port, of a SCBA. The pressure line 14 is preferably tubular with a lumen 16 being defined therein. The SCBA fitting will be valve controlled to permit selective exposure of the air contained within the air tank of the SCBA to the pressure line 14, particularly to the lumen 16.

The pressure line 14 terminates at a bleeder valve 18. The bleeder valve 18 is selectively adjustable between opened and closed states to permit air to escape from the pressure line 14 as required. In a normal operating position, the bleeder valve 18 will be closed to permit accurate reading of pressure within the pressure line 14. The bleeder valve 18 may be used to bleed air from the pressure line 14 where excess air is contained in the SCBA (e.g., in preparation for a breathing test).

A pressure gauge 20 is attached to the pressure line 14 to measure the pressure of air contained therein. It is preferred that the pressure gauge 20 include a transducer 22 and a display 24 for digitally showing the measured pressure level in the pressure line 14. In particular, it is preferred that the transducer 22 be in communication with the lumen 16 to mechanically detect pressure levels in the lumen 16 and to convert the mechanically-detected pressure levels into electrical signals. It is preferred that the pressure gauge 20 be a digital pressure gauge adapted to receive the electrical signals from the transducer 22 and to digitally display a pressure reading based on the electrical signals on the display 24, which is preferably a digital display. Any known transducer and digital pressure gauge may be utilized. It is preferred that the pressure gauge 20 be provided with a high level of accuracy, e.g., +/−1 psi, to permit highly accurate pressure readings of the pressure within the pressure line 14. It is further preferred that the pressure gauge 20 be capable of reading pressures of between 0-6,000 psi.

Figure 2:
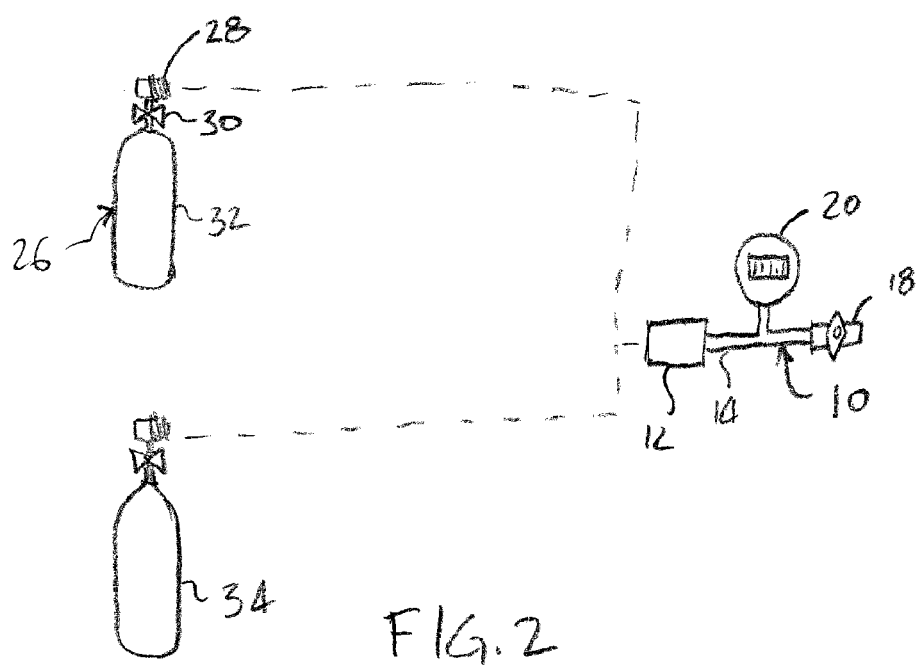
FIG. 2 is a schematic showing the subject invention useable with one or more SCBA's.

With reference to FIG. 2, during use, the air gauge assembly 10 is mounted to an at least partially filled SCBA 26 using the mounting member 12. By way of non-limiting example, the SCBA 26 may be a thirty-minute bottle (having an air volume intended for thirty minutes of use) or a forty-five minute bottle (having an air volume intended for forty-five minutes of use). The SCBA 26 may be provided with an air volume of approximately 1274-1835 liters at 4,500 psi. The SCBA 26 includes an air port 28 to which is mounted the mounting member 12. During mounting, the SCBA 26 is configured to have its valving 30 closed so that the air gauge assembly 10 is not exposed to any pressure from the air contained in the air tank 32 of the SCBA 26. Once mounted, the valving 30 of the SCBA 26 is manipulated to expose the air contained within the air tank 32 of the SCBA 26 to the air gauge assembly 10 via the mounting member 12. As such, pressurized air enters the lumen 16 of the pressure line 14 from the air tank 32 via the mounting member 12. With the bleeder valve 18 being closed, pressure in the pressure line 14 eventually comes into equilibrium with the pressure of the air in the air tank 32 of the SCBA 26. The pressure gauge 20 permits an accurate reading of the pressure contained in the pressure line 14 and, thus, provides an accurate reading of the volume of the air in the air tank 32. An accurate pressure reading can be obtained when equilibrium is achieved. Prior to equilibrium, the pressure readings may fluctuate. It is also noted that temperature may affect the pressure reading, particularly if one or more portions of the SCBA 26 are at elevated temperatures. The elevated temperature may cause an elevated pressure level and false indication of air volume level. All comparative pressure measurements should utilize a comparative temperature, e.g., ambient, to avoid possible misleading readings.

The technique described above permits an accurate pressure measurement to be obtained. Once obtained, a firefighter may be provided with the SCBA 26 and breathing tests may be conducted. After testing, the SCBA 26 pressure level may be once again obtained. The difference in pressure levels (which is an indicator of difference in air volume) may be used to accurately determine a firefighter's efficiency with a breathing technique or to determine in general their use of the SCBA.

The air gauge assembly 10 may be utilized to test the pressure of a plurality of SCBA's similar to the SCBA 26 described above. For comparative testing, it may be desired to set the same initial starting pressure levels across two or more SCBA's 26, 34, and so forth. Air pressure levels, and, thus, air volume levels, between the SCBA's may be equalized by bleeding off excess air using the bleeder valve 18 until the pressure readings of the SCBA's 26, 34 are the same. For example, if the pressure level of the SCBA 34 is higher than the pressure level of the SCBA 26, and with the air gauge assembly 10 mounted to the SCBA 34, the bleeder valve 18 may be opened and air released from the SCBA 34 until the pressure decreases (as indicted by the pressure gauge 20) to the desired level. Excess pressure in any of the SCBA's may be decreased in this manner. The SCBA's 26, 34 may then be provided to firefighters who undertake breathing exercises or tests with the devices. After the exercises are completed, the air gauge assembly 10 may be used to accurately measure pressure levels in the SCBA's 26, 34 to comparatively evaluate the breathing techniques of the firefighters. Advantageously, the firefighters may practice their breathing techniques to prolong the available supply of air with comparative data being obtainable to indicate efficacy.

It is preferred that all components of the air gauge assembly 10 be formed of robust and durable materials which will withstand repeated use under elevated pressures, including pressures of up to 6,000 psi.

What is claimed is:

1. A combination for comparative testing of breathing techniques of firefighters, said combination comprising:
   a first self-contained breathing apparatus having an air tank and an air port;
   a second self-contained breathing apparatus having an air tank and an air port; and,
   an apparatus comprising:
      a mounting member formed to mount onto an air port of a self-contained breathing apparatus;
      a pressure line extending from said mounting member having a lumen which is communicatable with the air port of the self-contained breathing apparatus with said mounting member being mounted thereto;
      a pressure gauge operatively connected to said pressure line to detect pressure levels in said lumen of said pressure line; and,
      a bleeder valve mounted to said pressure line being selectively adjustable between a first open state and a second closed state, wherein, with said mounting member being mounted to the air port of one of the self-contained breathing apparatuses, and with said bleeder valve being in said first open state, said lumen is in communication with the surrounding environment via said bleeder valve, and wherein, with said mounting member being mounted to the air port of one of the self-contained breathing apparatuses, and with said bleeder valve being in said second closed state, said lumen is isolated from the surrounding environment,
   wherein said apparatus is selectively mountable on said first and second self-contained breathing apparatuses, and wherein, with selective adjustment of said bleeder valve, the air volumes in said air tanks of said first and second self-contained breathing apparatuses may be manipulated to be substantially equal.

2. A combination as in claim 1, wherein said first and second self-contained breathing apparatuses are generally the same temperature when the air volumes are being manipulated to be substantially equal.

3. A combination as in claim 1, wherein the apparatus is hand-held and portable.

4. A combination as in claim 1, further comprising a transducer in communication with said lumen to mechanically detect pressure levels in said lumen and to convert the mechanically-detected pressure levels into electrical signals.

5. A combination as in claim 4, wherein the pressure gauge is a digital pressure gauge formed to receive said electrical signals from said transducer and to digitally display a pressure reading based on said electrical signals.

6. A method of comparative testing of breathing techniques of one or more firefighters, said method comprising:

provinding first and second self-contained breathing apparatuses;

providing an apparatus comprising:

a mounting member formed to mount onto an air port of a self-contained breathing apparatus;

a pressure line extending from said mounting member having a lumen which is communicatable with the air port of the self-contained breathing apparatus with said mounting member being mounted thereto;

a pressure gauge operatively connected to said pressure line to detect pressure levels in said lumen of said pressure line; and, a bleeder valve mounted to said pressure line being selectively adjustable between a first open state and a second closed state, wherein, with said mounting member being mounted to the air port of one of the self-contained breathing apparatuses, and with said bleeder valve being in said first open state, said lumen is in communication with the surrounding environment via said bleeder valve, and wherein, with said mounting member being mounted to the air port of one of the self-contained breathing apparatuses, and with said bleeder valve being in said second closed state, said lumen is isolated from the surrounding environment;

selectively manipulating the air volumes of said first and second self-contained breathing apparatuses utilizing the bleeder valve of said apparatus to have the air volumes therebetween be substantially equal;

conducting testing of breathing techniques of first and second firefighters utilizing said first and second self-contained breathing apparatuses; and, determining the pressure levels of the air in said first and second self-contained breathing apparatuses after the testing to evaluate the difference in the air volumes of said first and second self-contained breathing apparatuses before and after testing.

7. A method as in claim 6, wherein the apparatus is hand-held and portable.

8. A method as in claim 6, further comprising a transducer in communication with said lumen to mechanically detect pressure levels in said lumen and to convert the mechanically-detected pressure levels into electrical signals.

9. A method as in claim 8, wherein the pressure gauge is a digital pressure gauge formed to receive said electrical signals from said transducer and to digitally display a pressure reading based on said electrical signals.

* * * * *